US00PP23529P2

(12) United States Plant Patent
Kordes

(10) Patent No.: US PP23,529 P2
(45) Date of Patent: Apr. 16, 2013

(54) SHRUB ROSE PLANT NAMED 'KORHOPIKO'

(50) Latin Name: *Rosa hybrida*
Varietal Denomination: KORhopiko

(75) Inventor: Tim-Hermann Kordes, Klein-Offenseth Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/135,852

(22) Filed: Jul. 15, 2011

(51) Int. Cl.
*A01H 5/00* (2006.01)

(52) U.S. Cl. ..... Plt./107

(58) Field of Classification Search ..... Plt./107, Plt./108

See application file for complete search history.

*Primary Examiner* — Kent L Bell

(57) ABSTRACT

A new and distinct variety of rose with long lasting, novel hot pink flowers, and attractive foliage with excellent disease resistance. It exhibits vigorous growth, upright to bushy habit and abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORhopiko'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORhopiko'.

SUMMARY OF THE INVENTION

The new rose plant may be distinguished from its seed parent, an 'un-named seedling', by the following combination of characteristics:

1. The flower color of 'KORhopiko' is hot pink while the flower color of the seed parent is dark red.
2. The foliage of 'KORhopiko' is semi-glossy while the foliage of the pollen parent is very glossy.

The new rose plant may be distinguished from its pollen parent, an 'un-named seedling' by the following combination of characteristics:

1. 'KORhopiko' is moderately vigorous while the growth of the pollen parent is vigorous.
2. The petal count of 'KORhopiko' is semi-double while the petal count of the pollen parent is single.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORhopiko' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORhopiko' was selected in May, 2002 from the seedling beds to be asexually propagated for further evaluation. The first asexual propagation of 'KORhopiko' was done by budding to seedling understocks in July, 2002 at the inventor's nursery in Offenseth-Sparrieshoop, Germany.

This initial and other subsequent propagation conducted in controlled environments demonstrate that 'KORhopiko' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORhopiko'.

DETAILED BOTANICAL DESCRIPTION

The following is a description of 'KORhopiko', as observed growing in June, 2011 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORcasima', a rose variety from the same inventor described and illustrated in U.S. Plant Pat. No. 20,732 and issued on Feb. 9, 2010 are compared to 'KORhopiko' in Chart 1.

CHART 1

| Characteristic | 'KORhopiko' | 'KORcasima' |
|---|---|---|
| Flower bud size: | Upon opening; 35 mm (l) × 20 mm (w). | Upon opening; 20 mm (l) × 18 mm (w). |
| Peduncle Diameter: | 3-4 mm average. | 1-1.5 mm average. |
| Prickles: | 5 thorns per 10 cm of stem. | 15-20 thorns per 10 cm of stem. |

Parents:

*Seed parent*.—'Un-named seedling'.

*Pollen parent*.—'Un-named seedling'.

Classification:

*Botanical classification*.—*Rosa hybrida* 'KORhopiko'.

*Commercial classification*.—Shrub rose.

FLOWER AND FLOWER BUD

Blooming habit: Continuous.

Flower bud:

*Size*.—Upon opening, 35 mm in length from base of receptacle to end of bud and 20 mm diameter at its widest point.

*Bud form*.—Long. Pointed ovoid.

*Bud color*.—As sepals first unfold, bud color is Red Group 53B. When ¼ open, the upper surface of the petals is Red-Purple Group 58B, and the lower surface is Red-Purple Group 58B. Occasional guard petal has intonations in the center of Red Group 54C.

*Sepals*.—Color: Upper surface Green Group 148C. Lower surface Yellow-Green Group 146C. Intonations of Greyed-Purple Group 184C. Size: Average 25-30 mm (l)×8-10 mm (w). Base: Flat at union with receptacle. Shape: Weak foliaceous appendages on three of the five sepals. Sepal apex is generally cirrose. Surface texture: Upper side: Strongly pubescent. Lower surface: Lightly pubescent. Margins: Lightly pubescent with occasional stipitate glands.

Receptacle:

*Surface*.—Generally smooth with limited stipitate glands.

*Color*.—Yellow-Green Group 144A.

*Shape*.—Urn-shaped.

*Size*.—8 mm (h)×6 mm (w).

Peduncle:

*Surface*.—With stipitate glands.

*Length*.—20 to 30 mm average length.

*Diameter*.—3 to 4 mm average diameter.

*Color*.—Yellow-Green Group 144A.

*Strength*.—Moderately strong.

*Borne*.—Multiple flower buds per stem, generally 4 to 9.

Flower bloom:

*Fragrance*.—Light.

*Duration*.—On the plant 3 to 5 days, As a cut flower, 3 to 4 days. Senesced petals drop away cleanly.

*Size*.—Medium. When open, the average flower diameter is 50 to 75 mm and the average flower height is 20 mm.

*Form*.—Shape of flower when viewed from the side: Upon opening, upper part: Flat. Upon opening, lower part: Flat. Open flower, upper part: Flattened convex. Open flower, lower part: Convex.

Color:

*Upon opening, petals*.—Outermost petals: Outer Side: Red-Purple Group 53D. Inner Side: Red-Purple Group 57A. Innermost petals: Outer Side: Red-Purple Group 58B. Inner Side: Red-Purple Group 66A.

*Upon opening, basal petal spots*.—Basal petal spot, outermost petals: Outer Side: Yellow Group 2A. Inner Side: Yellow Group 2C. Basal petal spot, innermost petals: Outer Side: Green-Yellow Group 1B. Inner Side: Green-Yellow Group 1C.

*After opening, petals*.—Outermost petals: Outer Side: Red-Purple Group 57B. Inner Side: Red-Purple Group 57A. Innermost petals: Outer Side: Red-Purple Group 58B. Inner Side: Red-Purple Group 66A.

*After opening, basal petal spots*.—Basal petal spot, outermost petals: Outer Side: Yellow Group 4D. Inner Side: Yellow Group 4C. Basal petal spot, innermost petals: Outer Side: Yellow Group 4D. Inner Side: Yellow-Green Group 154D.

General tonality: On open flower Red-Purple Group 157A. No change in the general tonality at the end of the 3rd day. Afterwards, general tonality is Red-Purple Group 61B.

Petals:

*Petal count*.—Semi-Double. Average Range: Approximately 12-18 petals under normal conditions.

*Petal reflex*.—Petals reflex somewhat.

*Petal edge*.—Repand.

*Petal shape*.—Overall: Round with moderate undulation. Apex shape is obtuse. Shape of base is obtuse.

*Petal size*.—35-40 mm (l)×30-35 mm (w).

*Thickness*.—Average.

*Petal arrangement*.—Not Formal.

Petaloids: Usually a limited number present.

*Petaloid count*.—Average of 0-4 per flower.

*Petaloid size*.—Petaloids are 10-30 mm long and 4-10 mm wide.

*Petaloid color*.—Color of inner side is Red-Purple Group 66A. Color of outer side is Red Purple Group 57A.

*Petaloid texture*.—Satiny.

*Margins*.—Undulated, highly irregular in shape. Color of margins is Yellow-Orange Group 14C on one edge of margin.

*Petaloid shape*.—Most commonly deltoid, with some petaloids highly irregular. Apex: Acute. Base: Oblique.

Reproductive organs:

*Pistils*.—Abundant. Approximately 25 present. Stigmas: Location: Slightly inferior in position to anthers. Color: Greyed-Yellow Group 160B. Styles: Length: 6 mm long on average. Color: Greyed-Yellow Group 160C. Intonations of Greyed-Orange Group 176C.

*Stamens*.—Approximately 30 on average and regularly arranged. Anthers: Size: Average 3 mm long. Pollen: Generally present. Color: Yellow-Orange Group 18A. Filaments: Color: Yellow Group 3B. Length: 8-9 mm.

THE PLANT

Growth: Moderately vigorous.

Plant habit: Upright to bushy habit. When grown as a container plant, the average height of the plant is 40 cm and the average width is 40 cm. When grown as a field grown plant the average plant height is 75 cm and the average plant width is 65 cm.

Blooming: Recurrent.

Stems:

*Stem color*.—Young wood: Yellow-Green Group 146D. Older wood: Yellow-Green Group 146C.

*Stem surface*.—Young wood: Smooth. Older wood: Smooth.

Prickles: Present.

*Incidence*.—5 per 10 cm of stem.

*Size*.—Average length: 3-6 mm.

*Color*.—Immature prickles: Distal end colored Greyed-White Group 159A. Base of prickle Greyed-Orange Group 165B. Mature prickles: Greyed-Red Group 181C. Senescing to Greyed-Orange Group 165A.

*Anthocyanin*.—Not observed.

*Shape*.—Concave.

Leaves and leaflets: Normally 5 leaflets on normal leaves in middle of the stem.

*Venation pattern*.—Pyramidal net pattern.

*Leaf size*.—140 mm (l)×120 mm (w).

*Abundance*.—Average.

*Texture*.—Thick. Upper side of leaflet: Semi-glossy. Under side of leaflet: Matte.

*Color, mature foliage*.—Upper Leaf Surface: Yellow-Green Group 146A. Lower Leaf Surface: Green Group 146B.

*Color, juvenile foliage*.—Upper Leaf Surface: Yellow-Green Group 144A. Lower Leaf Surface: Yellow-Green Group 146C.

*Anthocyanin intonation*.—Present. Intonations of Greyed-Purple Group 144A on juvenile foliage.

Stipules:

*Size*.—On average 20 mm long. Average distance from distal tip to distal tip is 4 mm.

*Stipule color*.—Yellow-Green Group 146C.

*Anthocyanin*.—Greyed-Red Group 182B.

*Stipitate glands*.—On margins and upper side.

*Margins*.—Rough with stipitate glands.

*Shape*.—Apex: Apiculate. Base: Deltoid.

Petiole:

*Length*.—30-40 mm.

*Diameter*.—3 mm.

*Petiole color*.—Yellow-Green Group 146C.

*Underneath*.—Yellow-Green Group 146D.

*Margins*.—Rough with stipitate glands.

*Anthocyanin*.—Between Greyed-Red Group 182B and 182C.

*Prickles*.—Limited number of prickles on the underside.

*Stipitate glands*.—Present on margins and underside.

Petiole rachis:

*Length:* 15-25 mm on average.

*Diameter:* 2-3 mm on average.

*Color*.—Yellow-Green Group 146C. Intonations of Greyed-Orange Group 174A on juvenile tissue.

*Margins*.—With limited numbers of stipitate glands.

*Prickles*.—A few small prickles underneath.

*Stipitate glands*.—Generally present.

Leaflets:

*Size*.—Average size of the terminal leaflet is 75 mm (l)×45 mm (w).

*Shape*.—Entire leaflet: Ovate. Base: Obtuse. Apex: Acute.

*Margins*.—Serrated.

*Surface*.—Upper: Glossy. Lower: Matte Finish.

*Texture*.—Leathery.

*Arrangement*.—Odd Pinnate.

*Venation*.—Reticulate.

Hips/seed formation: None observed.

Winter hardiness: To date, the variety has been grown successfully in Zone 5.

Disease resistance: Excellent resistance to Powdery mildew (*Sphaerotheca pannosa*), blackspot (*Diplocarpon rosae*), and rust (*Phragmidium disciflorum*) diseases under normal growing conditions.

I claim:

1. A new and distinct variety of rose plant, as described and illustrated herein.

* * * * *

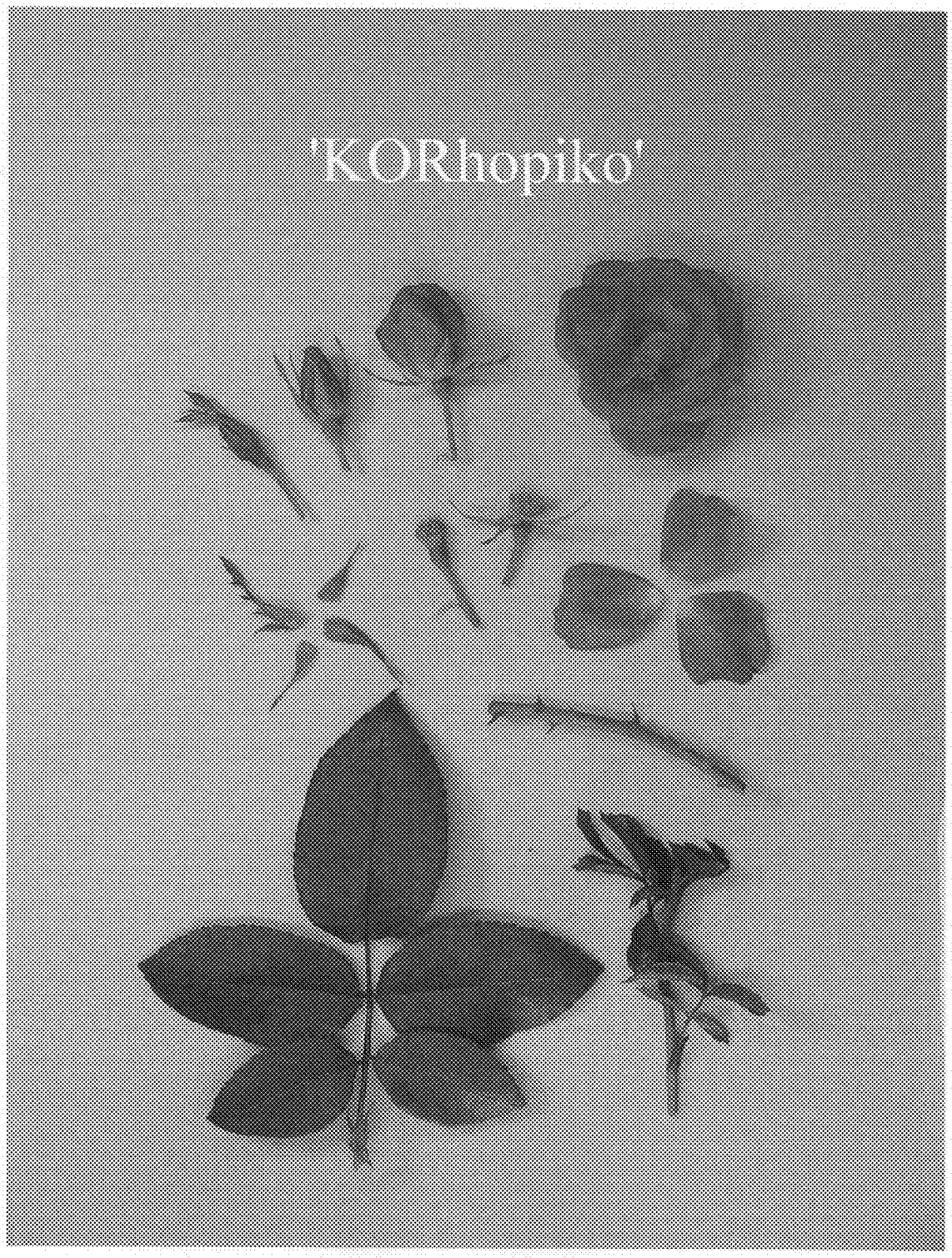
'KORhopiko'